United States Patent [19]
Nagaoka

[11] Patent Number: 5,782,781
[45] Date of Patent: Jul. 21, 1998

[54] ALL-IN-ONE GIRDLING BELT FOR LUMBAR AND COXA SUPPORT

[76] Inventor: Nobuo Nagaoka, 107-11 Hirata-cho, Hikone City, Shiga, Japan, 522

[21] Appl. No.: 637,990

[22] Filed: Apr. 25, 1996

[51] Int. Cl.$^6$ ............................. A61F 5/00; A61F 5/02
[52] U.S. Cl. ................................. 602/19; 128/101.1
[58] Field of Search ................ 602/19; 450/97–99, 450/155; 128/99.1, 100.1, 101.1; 482/105, 106

[56] References Cited

U.S. PATENT DOCUMENTS

| | | | |
|---|---|---|---|
| 1,063,922 | 6/1913 | Kendrick | 450/155 |
| 1,599,762 | 9/1926 | Guthrie et al. | 128/96.1 |
| 2,250,807 | 7/1941 | Lunney | 450/155 X |
| 2,695,019 | 11/1954 | Welter | 128/100.1 X |
| 2,730,096 | 1/1956 | Pease | 602/19 |
| 2,814,805 | 12/1957 | Blatt | 450/155 |
| 3,524,449 | 8/1970 | Peters | 450/155 X |
| 3,756,247 | 9/1973 | Hand | 450/155 X |
| 4,721,102 | 1/1988 | Pethybridge | 602/19 |
| 4,932,079 | 6/1990 | Bridgewater | 128/101.1 X |
| 4,985,937 | 1/1991 | Blackburn | 2/311 X |
| 5,038,760 | 8/1991 | Osborn | 602/19 |

*Primary Examiner*—Richard J. Apley
*Assistant Examiner*—Denise Pothier
*Attorney, Agent, or Firm*—John E. Halamka

[57] ABSTRACT

The object of the invention is to provide an elastic girdling belt which serves to secure and maintain in a normal condition the connective structure of the coxae and lumbar vertebrae which support the pelvis in the human body, thus correcting the figure and not only serving to cure daily life affecting diseases caused by abnormalities in those regions such as lumbago, neuralgia, or internal organ disorders, but also producing significant effects in the prevention of these diseases. The girdling belt, while easy to handle, also produces noticeable effects in shaping the body and raising the hips, and at the same time allowing the greatest to the subtlest range of motion required for daily life without producing tight, uncomfortable feeling.

32 Claims, 4 Drawing Sheets

Fig. 5.
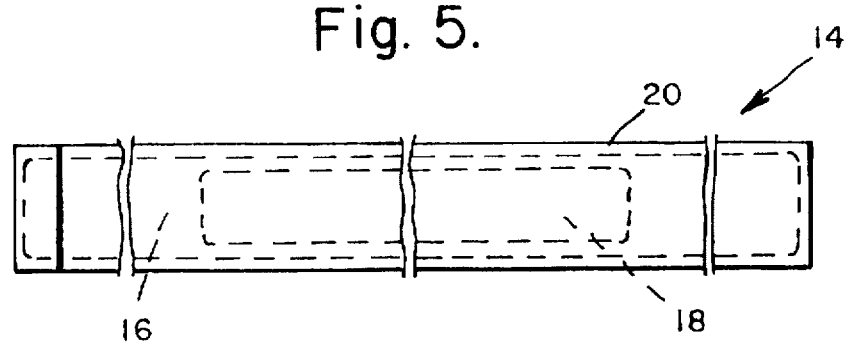
Fig. 6a.
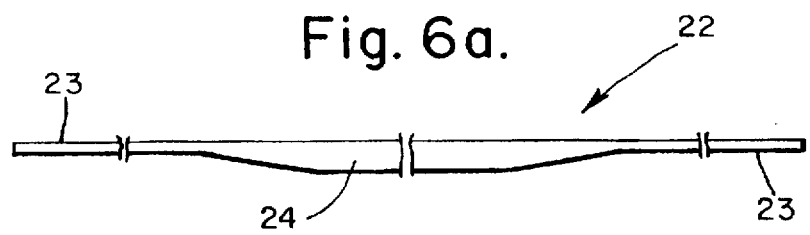
Fig. 6b.          Fig. 7a.          Fig. 7b.
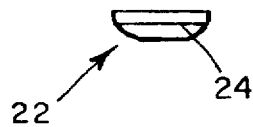 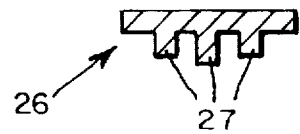 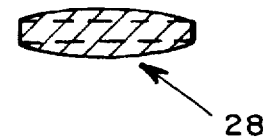
Fig. 7c.
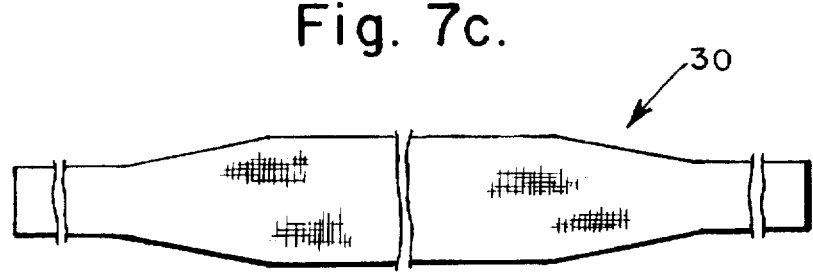

Fig. 8.
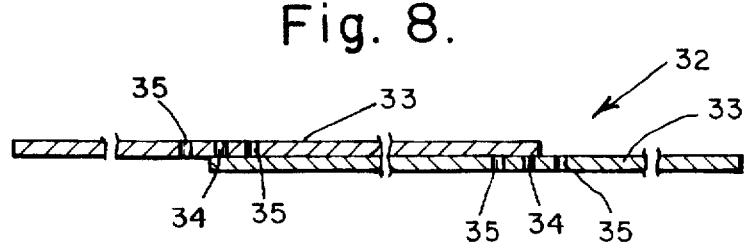
Fig. 9.
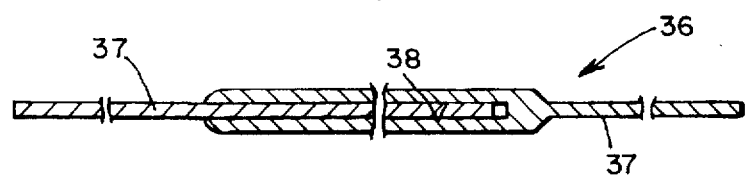
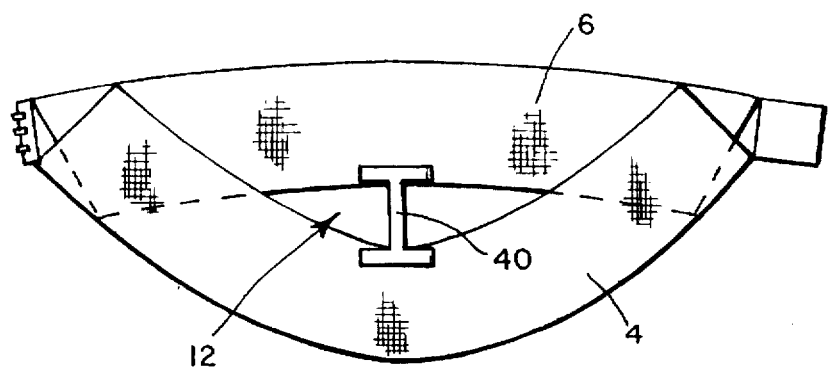
Fig. 10.
Fig. 11.
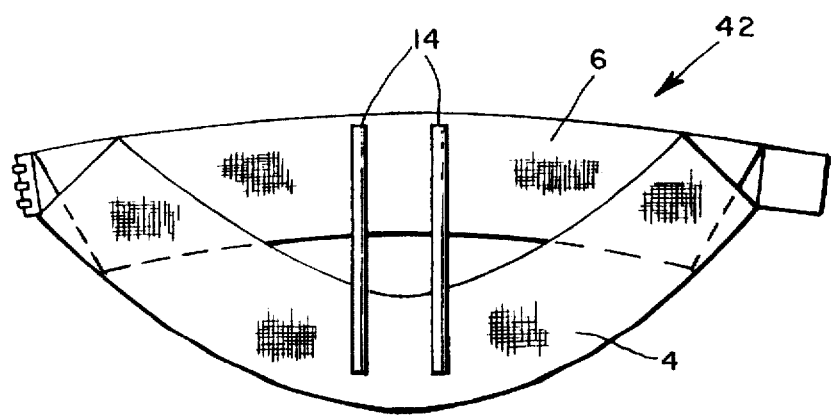

ALL-IN-ONE GIRDLING BELT FOR LUMBAR AND COXA SUPPORT

BACKGROUND

The present invention details an all-in-one girdling belt which supports the lumbar vertebrae and the coxae (this device hereinafter shall be referred to as the Belt). The Belt is designed to secure and stabilize the connective structure of the coxae and lumbar vertebrae in a natural configuration in order to lend support to the pelvis. The employment of the Belt facilitates in correcting structural ailments in the pelvic region and also serves to shape the body, especially in achieving significant results by producing shapely hips.

In the past, various products including corsets and belts have been utilized to correct or prevent abnormal curvatures or distortions in the lumbar vertebrae. These abnormalities can lead to sundry diseases such as lumbago, neuralgia, or disorders of internal organs. Some of the products produced consist of soft material, others hard; some are wide, others narrow. Each product has its own merits and demerits: a wide belt, designed primarily to immobilize the lumbar vertebrae, limits movement like a clamp; and a narrow belt, because it often slips up and down, does not provide sufficient steadiness.

No corsets or belts have ever been developed for specialized use on the coxae, except for a method developed and used in Japan that consists of taking rubber tubes from bicycle tires and wrapping them tightly around the coxae. This method is effective for alleviating pains during stretching and bending exercises; however, the rubber tubes prove impractical for daily use because they are insecurely fixed and hamper freedom of walking.

A different girdle device recently produced in Japan features a belt designed to tightly encircle the coxae. The drawback of this product is that it is designed as a woman's undergarment for figure control, and men are most unlikely to use it. Because the femoral region varies from person to person in either sex, a girdle like this will not allow the user to wear it for a long time, especially if sitting for an extended period of time which increases the pains and uneasiness experienced around the femoral region caused by the compression of the belts.

To date, no conventional method has ever succeeded in comfortably providing a constant and secure girdle for the coxae and lumbar vertebrae simultaneously. We feel that the human body deserves such a device that would act simultaneously and securely on both regions of the body instead of separately.

Brief description of the drawings

FIG. 5 is a top view, partially interrupted, of the bridging strap when inserted into the sheath.

FIG. 6a is a front view of another embodiment of the bridging strap to be used in the Belt. FIG. 6b is its side view.

FIG. 7a is a side view of the vertical section of an alternative embodiment of the bridging strap to be used in the Belt. FIG. 7b is a side view of the vertical section of yet another version of the bridging strap used in the Belt. FIG. 7c is a top view, partially interrupted, of the two bridging straps.

FIG. 8 is a front view, partially interrupted, of the vertical section of one more embodiment of the bridging strap to be used in the Belt.

FIG. 9 is a front view, partially interrupted, of the vertical section of another alternative embodiment of the bridging strap to be used in the Belt.

FIG. 10 is a front view of another preferred embodiment of the Belt.

FIG. 11 is a front view of yet another preferred embodiment of the Belt.

Figure 1:
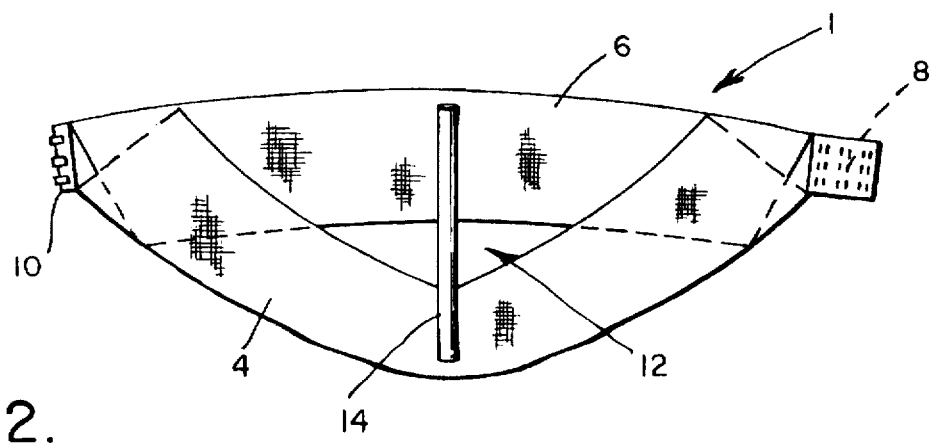
FIG. 1 is a front view of the inward side of the Belt, a preferred embodiment of the invention.

1, 42, 44, 46, and 54 indicate the Belt.
2 indicates the human body.
3 indicates the buttocks.
4, 48, and 56 indicate the belt encircling the coxae.
5 indicates the waist.
6, 50, and 58 indicate the belt encircling the lumbar vertebrae.
8, 10, and 60 indicate the closing device.
12 indicates the gap.
14, 22, 26, 28, 30, 32, 36, and 40 indicate the bridging strap.
16 indicates the flexible material component of the bridging strap.
18 indicates the elastic component of the bridging strap.
20 indicates the sheath enclosing the bridging strap core.
23 indicates both ends of the plastic strap.
24 indicates the middle part of the plastic strap.
27 indicates fins.
28 indicates the barrel shape.
33 and 37 indicate a pair of the linking mates making up the bridging strap.
34 indicates pins.
35 indicates holes corresponding to pins.
38 indicates the sheathing container space.
52 indicates the detach-and-slide closing device.

DETAILED DESCRIPTION OF THE INVENTION

Ever since humans evolved from four-legged animals and started walking upright on two feet, we have experienced many diseases associated with upright posture such as lumbago, neuralgia, weakening of eyesight, or disorders of internal organs. The entire force of the weight of humans became concentrated on two legs rather than four. In terms of the human skeletal structure, the femurs support the heaviest parts of the body including the vertebral column erected upon the pelvic girdle, the back, the arms, and the head.

The vertebral column breaks down into 24 vertebrae—5 lumbar, 12 thoracic, and 7 cervical—and the whole column is formed by piling up vertebrae on top of one another. Any imbalance in supporting the column may cause an abnormal curvature or deformity in the vertebral column which may lead to the before mentioned disorders.

The vertebral column is maintained in an erect posture and usually does not curve abnormally as long as the coxae—joints articulating the pelvis to the femurs—are operating normally. Disorders or diseases inside or in close proximity to the vertebral column may also lead to abnormal curvatures, deformities, or shears in the column resulting in an unbalanced coxa. Regardless of the cause, any condition that produces an abnormally stiff or loose joint may lead to diseases or disorders in that location. The afflicted parts, be they stiff or loose, abnormally curved or deformed, can be corrected with amazing results when a device that holds the coxae and lumbar vertebrae tight as one whole pelvic area.

There are many belts available that encircle the lumbar vertebrae, but no belts have ever been developed that properly support the coxae. Needless to mention, a device that combined support for both the lumbar and the coxae simultaneously has never been realized. Until now, that is.

We now present the All-in-one Girdling Belt for Lumbar and Coxa Support. The effectiveness of the Belt has been ascertained through trial by experiment by many people including the author. The development of the Belt is the result of our efforts to create a product the likes of which has never been successfully completed before; namely, a belt that gives steady support to the coxae lying below the pelvis while simultaneously lending support to the lumbar vertebrae lying above the pelvis. After extensive research, we have created a product that treats and prevents an extensive array of ailments including lumbago, neuralgia, and internal organ disorders. The Belt also can easily be worn for extended periods of time in comfort and provides the wearer with a more shapely figure.

A detailed description of the Belt is given in the following referring to attached FIGS. 1–14.

Figure 2:
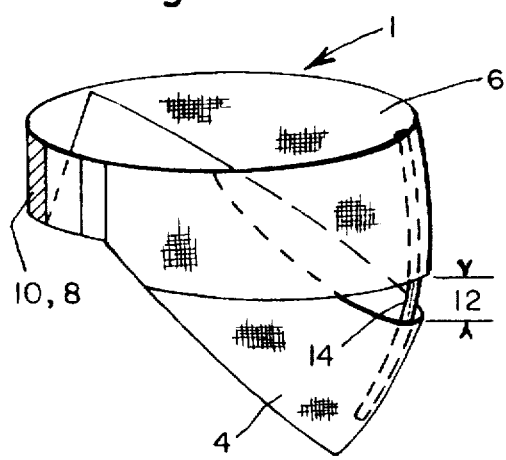
FIG. 2 is an oblique view of the Belt.
Figure 3:
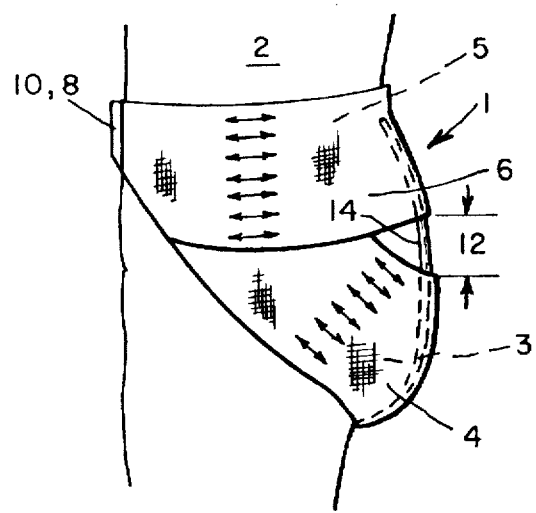
FIG. 3 is a side view of the Belt while worn on the body.
Figure 4A:
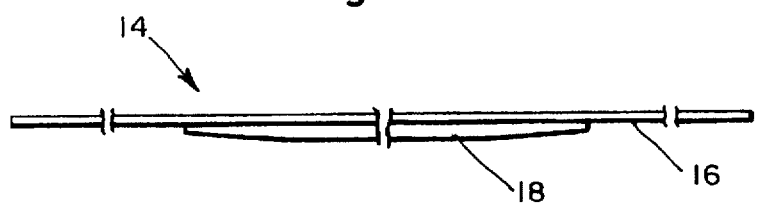
FIG. 4a is a front view, partially interrupted, of a preferred embodiment of the bridging strap used in the Belt.
Figure 4B:
FIG. 4b is its side view.

As shown in FIGS. 1, 2, and 3, the Belt is comprised of the COXA BELT (4), elastic and tightly encircling the hip (3) while covering the lower part of the pelvis of the body (2) including the coxae; the LUMBAR BELT (6), elastic and binding tight around the waist (5) covering the upper part of the pelvis and the lumbar vertebrae; the CLOSING DEVICES (8, 10) which connect the coxa belt to the lumbar belt and serve as fasteners to close the belts together at both sides; and the BRIDGE (the bridging strap 14) which extends across the space gap (12) forming at the center between the two belts (4, 6), thus controlling the motion of the gap.

The coxa belt (4) and the lumbar belt (6) may be composed of a plain strap of solid rubber or similar material, or made of a fabric knitted or woven from elastic fibers which preferably are more densely used lengthwise to retain more elasticity lengthwise than widthwise. Either elastic or non-elastic fibers may be used widthwise in the belts.

The lengths of the two belts (4, 6) should be as short as possible to provide sufficient binding force to suit the standard body size. The coxa belt (4) may retain a binding force as strong or stronger than the lumbar belt (6). There are no specifications regarding the relation between the binding forces of the two belts.

The widths of the two belts (4, 6) may be the same or they may differ. Also, the width of each belt as it runs along the length may vary. For example, the width of the coxa belt may be wider at the middle part of the length that covers the buttocks (3). There is no specific rule in setting the width, but for standard adult size, both belts should be wider than 8 cm with a general recommended length of 12 to 15 cm.

A preferred embodiment of the invention has the two belts (4, 6) stitched and fastened together by overlapping the two ends at a certain angle to form a unified and dimensional unit. The range of preferable angles extends from 25 to 50 degrees with a 35 degree angle as the most recommended. FIG. 1 illustrates the areas of the two belts which are suggested to be overlapped and stitched together.

One part of the two-part closing device (8, 10) is attached to each of the two overlapped and stitched ends that join the two belts (4, 6) together. A preferred embodiment of the closing device is positioned where the two belts are best balanced in regards to tension. The closing device consists of hooks (10) on one end and loops (8) on the other end. A preferred embodiment of the closing device has multiple rows of eyes and hooks allowing for various fastening positions. The closing device permits the simultaneous changing of tensions of the two belts. Other forms of closing devices may be employed such as Velcro fasteners, buckles, or sashes.

The coxa belt (4) and lumbar belt (6) are attached at both ends but are otherwise separated creating an adjustable gap (12) between the two belts. The preferred embodiment of the invention has the bridge (14) connecting the two belts by stretching across the center of the gap. This bridge limits the span of the gap from 2 cm to 15 cm thus allowing for variations in users' body types and sizes.

The bridge is designed so that the middle part—the two-layered area with the soft material strap (16) and the elastic material strap (18) combined—is capable of stretching elastically against the bending force. On the other hand, it is formed rigidly enough not to break against the axial stress. Each end of the strap consists of a soft-material (16) without the elastic material strap (18) and is capable of bending freely against applied force.

Both ends of the bridge are sewn onto the two belts (4, 6) via the linking cloth sheath (20) which limits, to a certain extent, the gap or movement between the two belts. The movement of the bridge is restricted since both ends are fastened to the belts. The middle section of the bridge, while not fastened to the belts, is rigid enough to maintain its structure.

How to put on the Belt:
1. Hold one half of the closing device (8, 10) in each hand.
2. Place the coxa belt (4) around the hips.
3. Bring each half of the closing device up to the abdomen while drawing the coxa belt around the hips and the lumbar belt (6) around the lumbar region.
4. Pull the ends of both belts tight with sufficient binding force and fasten the closing device.

Adjustments:
1. Make sure that the bridge is applied to the central axial line extending from the spinal column to the anal groove.
2. Make sure that the coxa belt (4) is properly positioned around the hips.
3. Make sure that the lumbar belt (6) is properly positioned around the upper part of the pelvis and the lumbar vertebrae.
4. Adjust the two belts so that they closely fit the body without discomfort.
5. Change the fastening position of the closing device (8, 10) if the binding force of the two belts is not felt to be appropriate.

The handling and usage of the Belt is very easy. The belt may be worn next to the skin or over one's underwear, producing the same effects in either case. Different parts of the body may be simultaneously supported with the two elastic belts (4, 6).

The lumbar belt (6) is designed to lend support to the sacrum in the middle-upper part of the pelvis and the 5th lumbar vertebra (and the 3rd and 4th vertebrae when the belt is wider), and to encircle around the waist toward the front abdomen, serving as a lumbar girdle.

The coxa belt (4) is designed to wrap and support the lower part of the buttocks (3), the middle-lower part of the pelvis, and the coxae. The Belt extends diagonally up to the front abdomen. Girdling support of this nature holds certain protective and corrective efficacy against various diseases such as lumbago, neuralgia, internal organ disorders, gastroptosis, weakening of eyesight, as well as correcting posture. The Belt, being sufficiently wide and closely fitting an extensive area of the body surface, significantly contributes to achieving a shapely body since the Belt helps to correct the figure instead of causing deformities; specifically, the Belt contributes to a slim waist and raises the hips. And besides contributing to body shaping, the Belt has yet another advantage: the structure of the Belt allows the wearer to leave his or her home, exercise, and even perform physical labor. While certain preferred embodiments of the invention have been disclosed in detail, it is necessary to say that the invention is not limited to the above-mentioned embodiments.

Further alternative embodiments or modifications of the invention

Variations on the bridge (14)

The soft material strap (16) of the bridge (14) may be made of plastic such as polyethylene, or other flexible material. The elastic strap (18) is made of plastic such as acrylic resin or a similarly elastic material.

FIG. 6 illustrates a bridging strap (22) designed to perform the same function as provided by the bridge. It is composed of a single material and formed thinner at both ends and thicker in the middle. The material used herein may be a synthetic plastic such as high density polyethylene.

FIG. 7a illustrates a bridging strap (26) having fins (27) in its middle; FIG. 7b illustrates another strap (28) with a barrel-shaped middle part; and FIG. 7c illustrates another embodiment of a bridging strap (30) with a wide middle trunk. The middle parts of these three bridging straps perform the same function.

FIG. 8 illustrates another version of the bridging strap (32) made up of a pair of mating straps (33), one of which has a number of pins (34) which fit into corresponding holes in the other strap. This structure of the bridging strap permits the wearer to change the length of the strap according to one's body size. Also, in this strap, the middle part is rigid while the ends remain flexible.

FIG. 9 illustrates another bridging strap (36) consisting also of two mating partners. One mate slides into or out of the other mate in a telescoping motion. The telescoping function of the strap permits the wearer to frequently bend and stretch the waist, allowing for an extensive expansion and contraction of the skin extending from the upper part of the posterior waist to the buttocks without obstructing the body motion and without disturbing the positioning of the two belts.

While various embodiments of the bridging strap to be used on the Belt have been disclosed in detail, the following lists the essential functions required of all bridging straps.

Figure 12:
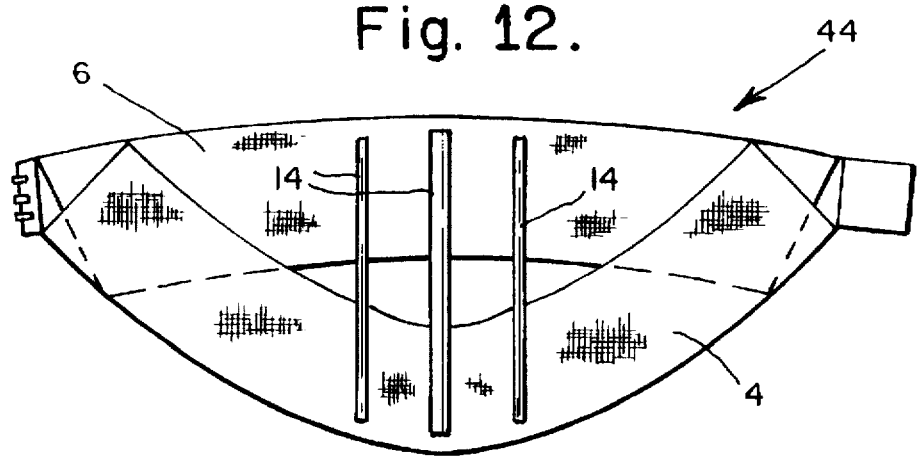
FIG. 12 is a front view of another alternative embodiment of the Belt.

1. Linking and fastening the two belts (4, 6) at the posterior waist region to create a certain gap size so that the belts do not slide upward or downward while in use. FIG. 11 demonstrates version 42 of the invention having two pieces of the bridge (14) running parallel across the gap at the middle of the two belts to link them. FIG. 12 demonstrates version 44 of the invention having three pieces of the bridge (14) also running parallel across the gap near the middle of the two belts. The number of bridging straps used in the invention is not to be specified, and the sizes may vary when more than one strap is used.
2. Resisting buckling in the middle of the bridging strap when subjected to a compressive force.
3. At the very least, capable of restricting the gap or the movement between the two belts (4, 6). FIG. 10 demonstrating version 40 of the bridging strap is the minimum necessary length to restrict the gap (12). The bridging strap may be attached by an adhesive or be welded directly or indirectly to the two belts, rather than being sheathed and sewn to the belts.

Variations of the lumbar belt (4) and the coxa belt (6)

Figure 13:
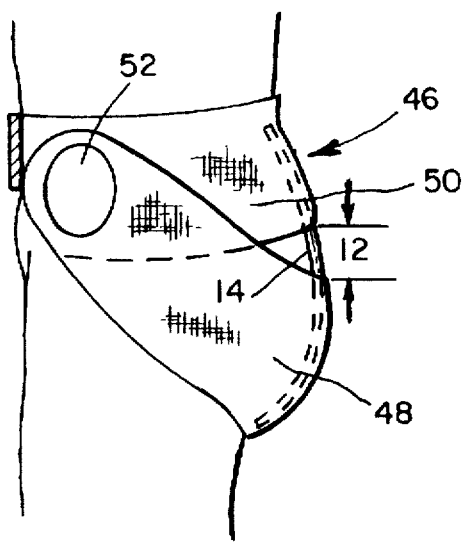
FIG. 13 is a side view of yet another version of the Belt.

FIG. 13 illustrates anther version of the Belt in which the coxa belt (48) is linked to the lumbar belt (50) with a detachable fastener (52) allowing the wearer to select the angle that fits the best.

Figure 14:
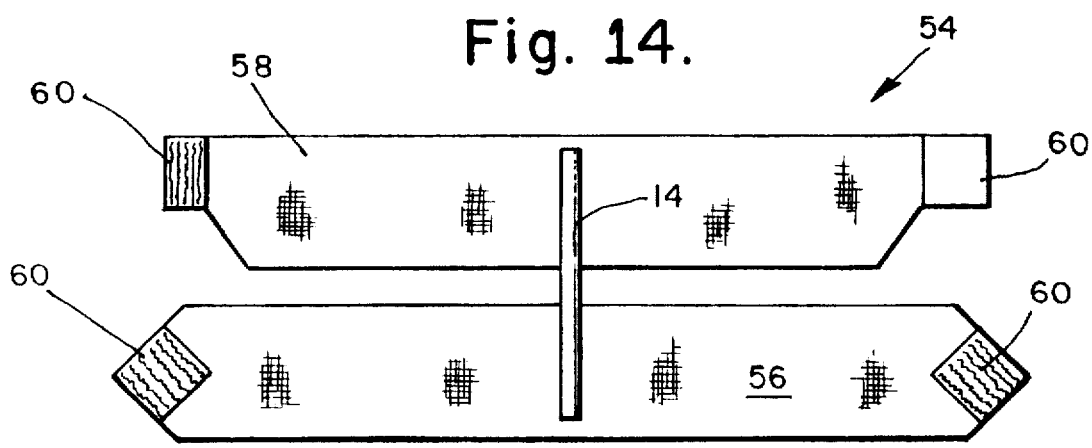
FIG. 14 is a front view of one more version of the Belt.

FIG. 14 illustrates another version of the invention having the two belts (54, 56) fastened together at the front abdomen by Velcro (60) attached to each end of the belts.

In both versions, the binding force of the two belts may be adjusted to achieve the best fitting. Also, in both versions, the two belts are detachable but the relative positions of the belts remain stabilized by the bridge (14).

While various preferred embodiments of the Belt have been described and illustrated, it is to be understood that the invention is by no means limited to such specific embodiments so far illustrated. Essentially, the two belts are required to retain a level of elasticity suitable to bind the human body. To a certain extent, a higher level is preferable. The lumbar belt and/or coxa belt may be composed of a plate of an elastic material such as rubber. Or the surface of the isotropic plate may be affixed with an elastic cloth. It is not necessary that the two belts be made entirely of elastic materials. The belts may consist of a combination of two materials—elastic and non-elastic—alternately arranged. The two belts may be designed so that their lengths are adjustable, although the closing device may not permit the wearer to change the fastening position. The lumbar belt and/or coxa belt may include magnetic or chiropractic devices for therapeutic effects. Also, a pocket may be built-in for holding such things as a warming device.

The invention may embody various versions by adopting various improvements, modifications, or transformations based on the knowledge of the manufacturer within the scope of the spirit of the invention. The spirit of this invention includes the following points:

1. The Belt serves to maintain the lumbar vertebrae in an erect and natural position above the pelvis, and thereby lends support to the upper part of the body and at the same time prevents various related diseases. Furthermore, because the Belt integrates two belts which simultaneously encircle and support both the lumbar region and the coxa region, the coxa region as well as the lumbar region are both firmly held in a natural position.
2. The corrective functions of the Belt also serve to produce curative effects on diseases which are caused by abnormalities in the lumbo-sacral region such as lumbago, neuralgia, or internal organ disorders.
3. Although the lumbar and coxa regions of the body feature difficult curves and a wide range of twisting movements, the Belt permits active movement of the body without the displacement of the two belts thanks in large part to the bridging strap connecting the two belts.
4. The Belt will never cut into the lower part of the abdomen or the inside of the thigh whether in standing or sitting position; the Belt can be adjusted to suit everybody.
5. The middle part of the bridge, structured to maintain its rigidity against a compressive force, prevents the two belts from displacement when they are subjected to a sliding stress following bending and stretching exercises by the body.

6. The flexible ends of the bridge permit no sense of unsteadiness because they are capable of being flexed and stretched according to the movements of the body.

What is claimed is:

1. A girdling belt device to tightly bind the abdomen by fitting around the waist and under the buttocks of the user keeping the coxae and lumbar vertebrae in place thereby releasing strain which may be causing pain comprising:
   (a) a coxa belt having a first end, a second end, an upper edge and a lower edge, preselected portions being fabricated of elastic material, adapted to encircle and be binding around the buttocks, said lower edge of said coxa belt covering connective structure of the coxae vertebrae lying at the lower part of the spinal column which is connected to the human pelvis;
   (b) a lumbar belt having a first end, a second end, an upper edge and a lower edge, preselected portions being fabricated of elastic material, adapted to encircle and be binding around the waist including the upper part of the pelvis and lumbar vertebrae, said lower edge of said lumbar belt being spaced apart from said upper edge of said coxa belt thereby forming a gap;
   (c) a closing means which fastens together said first end and second end of said coxa belt and said first end and second end of said lumbar belt;
   (d) a at least one bridging strap means, bridging across said gap extending between said coxa belt and said lumbar belt at or near the center of each said belt.

2. A girdling belt device in accordance with claim 1 in which said at least one bridging strap means linking said coxa belt to said lumbar belt at or near the center of each said belt are fabricated of a preselected number of layered materials whereby the middle of said bridging strap means exhibits rigidity against a compressive force and preselected ends of said bridging strap means is flexible.

3. A girdling belt device as described in claim 2 and in which that portion of said at least one bridging strap means, linking said coxa belt to said lumbar belt at or near the center of each said belt and extending only over the vertical range of the gap between said belts is fabricated of preselected material whereby said portion exhibits rigidity against a compressive force over said gap.

4. A girdling device as described in claim 3 and further characterized by the unification of said coxa belt, and said lumbar belt, by the placement of said first end of said coxa belt overlapping said first end of said lumbar belt and said second end of said coxa belt overlapping said second end of said lumbar belt forming a preselected angle between said coxa belt and said lumber belt, said closing means being attached to and securing said overlapping ends together whereby said secured, overlapping ends may be fastened together after said unified coxa belt and lumbar belt are positioned around the coxa, buttocks and waist of the user.

5. A girdling belt device as described in claim 4 in which that portion of said at least one bridging strap means linking said coxa belt to said lumbar belt at or near the center of each said belt is further characterized by having adjustable means to permit the adjustment of the longitudinal length of said portion across said gap between said coxa belt and said lumbar belt whereby the user may obtain optimum fitting.

6. A girdling belt device as described in claim 5 in which said coxa belt and said lumbar belt retain a preselected amount of horizontal elasticity and a preselected amount of longitudinal elasticity under the condition of being placed on the body of the user.

7. A girdling belt device as described in claim 4 in which said coxa belt and said lumbar belt retain a preselected amount of horizontal elasticity and a preselected amount of longitudinal elasticity under the condition of being placed on the body of the user.

8. A girdling belt device as described in claim 3 in which that portion of said at least one bridging strap means linking said coxa belt to said lumbar belt at or near the center of each said belt is further characterized by having adjustable means to permit the adjustment of the longitudinal length of said portion across said gap between said coxa belt and said lumbar belt whereby the user may obtain optimum fitting.

9. A girdling belt device as described in claim 8 in which said coxa belt and said lumbar belt retain a preselected amount of horizontal elasticity and a preselected amount of longitudinal elasticity under the condition of being placed on the body of the user.

10. A girdling belt device as described in claim 3 in which said coxa belt and said lumbar belt retain a preselected amount of horizontal elasticity and a preselected amount of longitudinal elasticity under the condition of being placed on the body of the user.

11. A girdling device as described in claim 2 and further characterized by the unification of said coxa belt, and said lumbar belt, by the placement of said first end of said coxa belt overlapping said first end of said lumbar belt and said second end of said coxa belt overlapping said second end of said lumbar belt forming a preselected angle between said coxa belt and said lumber belt, said closing means being attached to and securing said overlapping ends together whereby said secured, overlapping ends may be fastened together after said unified coxa belt and lumbar belt are positioned around the coxa, buttocks and waist of the user.

12. A girdling belt device as described in claim 11 in which that portion of said at least one bridging strap means linking said coxa belt to said lumbar belt at or near the center of each said belt is further characterized by having adjustable means to permit the adjustment of the longitudinal length of said portion across said gap between said coxa belt and said lumbar belt whereby the user may obtain optimum fitting.

13. A girdling belt device as described in claim 12 in which said coxa belt and said lumbar belt retain a preselected amount of horizontal elasticity and a preselected amount of longitudinal elasticity under the condition of being placed on the body of the user.

14. A girdling belt device as described in claim 11 in which said coxa belt and said lumbar belt retain a preselected amount of horizontal elasticity and a preselected amount of longitudinal elasticity under the condition of being placed on the body of the user.

15. A girdling belt device as described in claim 2 in which that portion of said at least one plurality of bridging strap means linking said coxa belt to said lumbar belt at or near the center of each said belt is further characterized by having adjustable means to permit the adjustment of the longitudinal length of said portion across said gap between said coxa belt and said lumbar belt whereby the user may obtain optimum fitting.

16. A girdling belt device as described in claim 15 in which said coxa belt and said lumbar belt retain a preselected amount of horizontal elasticity and a preselected amount of longitudinal elasticity under the condition of being placed on the body of the user.

17. A girding belt device as described in claim 2 in which said coxa belt and said lumbar belt retain a preselected amount of horizontal elasticity and a preselected amount of longitudinal elasticity under the condition of being placed on the body of the user.

18. A girdling belt device as described in claim 1 and in which that portion of said at least one bridging strap, means linking said coxa belt to said lumbar belt at or near the center of each said belt and extending only over the vertical range of the gap between said belts is fabricated of preselected material whereby said portion exhibits rigidity against a compressive force over said gap.

19. A girdling device as described in claim 18 and further characterized by the unification of said coxa belt, and said lumbar belt, by the placement of said first end of said coxa belt overlapping said first end of said lumbar belt and said second end of said coxa belt overlapping said second end of said lumbar belt forming a preselected angle between said coxa belt and said lumber belt, said closing means being attached to and securing said overlapping ends together whereby said secured, overlapping ends may be fastened together after said unified coxa belt and lumbar belt are positioned around the coxa, buttocks and waist of the user.

20. A girdling belt device as described in claim 19 in which that portion of said at least one bridging strap means linking said coxa belt to said lumbar belt at or near the center of each said belt is further characterized by having adjustable means to permit the adjustment of the longitudinal length of said portion across said gap between said coxa belt and said lumbar belt whereby the user may obtain optimum fitting.

21. A girdling belt device as described in claim 20 in which said coxa belt and said lumbar belt retain a preselected amount of horizontal elasticity and a preselected amount of longitudinal elasticity under the condition of being placed on the body of the user.

22. A girdling belt device as described in claim 19 in which said coxa belt and said lumbar belt retain a preselected amount of horizontal elasticity and a preselected amount of longitudinal elasticity under the condition of being placed on the body of the user.

23. A girdling belt device as described in claim 18 in which that portion of said at least one bridging strap means linking said coxa belt to said lumbar belt at or near the center of each said belt is further characterized by having adjustable means to permit the adjustment of the longitudinal length of said portion across said gap between said coxa belt and said lumbar belt whereby the user may obtain optimum fitting.

24. A girdling belt device as described in claim 23 in which said coxa belt and said lumbar belt retain a preselected amount of horizontal elasticity and a preselected amount of longitudinal elasticity under the condition of being placed on the body of the user.

25. A girdling belt device as described in claim 18 in which said coxa belt and said lumbar belt retain a preselected amount of horizontal elasticity and a preselected amount of longitudinal elasticity under the condition of being placed on the body of the user.

26. A girdling device as described in claim 1 and further characterized by the unification of said coxa belt, and said lumbar belt, by the placement of said first end of said coxa belt overlapping said first end of said lumbar belt and said second end of said coxa belt overlapping said second end of said lumbar belt forming a preselected angle between said coxa belt and said lumber belt, said closing means being attached to and securing said overlapping ends together whereby said secured, overlapping ends may be fastened together after said unified coxa belt and lumbar belt are positioned around the coxa, buttocks and waist of the user.

27. A girdling belt device as described in claim 26 in which that portion of said at least one bridging strap means linking said coxa belt to said lumbar belt at or near the center of each said belt is further characterized by having adjustable means to permit the adjustment of the longitudinal length of said portion across said gap between said coxa belt and said lumbar belt whereby the user may obtain optimum fitting.

28. A girdling belt device as described in claim 27 in which said coxa belt and said lumbar belt retain a preselected amount of horizontal elasticity and a preselected amount of longitudinal elasticity under the condition of being placed on the body of the user.

29. A girdling belt device as described in claim 26 in which said coxa belt and said lumbar belt retain a preselected amount of horizontal elasticity and a preselected amount of longitudinal elasticity under the condition of being placed on the body of the user.

30. A girdling belt device as described in claim 1 in which that portion of said at least one bridging strap means linking said coxa belt to said lumbar belt at or near the center of each said belt is further characterized by having adjustable means t o permit the adjustment of the longitudinal length of said portion across said gap between said coxa belt and said lumbar belt whereby the user may obtain optimum fitting.

31. A girdling belt device as described in claim 30 in which said coxa belt and said lumbar belt retain a preselected amount of horizontal elasticity and a preselected amount of longitudinal elasticity under the condition of being placed on the body of the user.

32. A girdling belt device as described in claim 1 in which said coxa belt and said lumbar belt retain a preselected amount of horizontal elasticity and a preselected amount of longitudinal elasticity under the condition of being placed on the body of the user.

* * * * *